United States Patent
Eriksson (10) Patent No.: US 10,350,105 B2
(45) Date of Patent: Jul. 16, 2019

(54) WRIST-HAND-FINGER ORTHOSIS

(71) Applicant: MediRoyal Nordic AB, Sollentuna (SE)

(72) Inventor: Thomas Eriksson, Bromma (SE)

(73) Assignee: MEDIROYAL NORDIC AB, Sollentuna (SE)

( * ) Notice: Subject to any disclaimer, the term of this patent is extended or adjusted under 35 U.S.C. 154(b) by 770 days.

(21) Appl. No.: 14/859,575

(22) Filed: Sep. 21, 2015

(65) Prior Publication Data

US 2016/0081843 A1 Mar. 24, 2016

(51) Int. Cl.
*A61F 5/00* (2006.01)
*A61F 5/058* (2006.01)
*A61F 5/01* (2006.01)

(52) U.S. Cl.
CPC .......... *A61F 5/05866* (2013.01); *A61F 5/012* (2013.01); *A61F 5/0118* (2013.01); *A61F 5/05816* (2013.01)

(58) Field of Classification Search
CPC ...... A61F 5/013; A61F 5/012; A61F 5/05816; A61F 5/05866; A61F 5/0118; A61F 2005/0155; A61F 2005/0146
See application file for complete search history.

(56) References Cited

U.S. PATENT DOCUMENTS

| | | |
|---|---|---|
| 3,942,522 A | 3/1976 | Wilson |
| 5,020,515 A | 6/1991 | Mann et al. |
| 5,056,504 A | 10/1991 | Mann |
| D333,520 S | 2/1993 | Mann |
| 5,383,827 A | 1/1995 | Stern |
| 5,437,620 A * | 8/1995 | Shelly ............... A61F 5/05866 601/40 |
| D362,914 S | 10/1995 | Mann |
| 5,466,202 A | 11/1995 | Stern |
| 5,531,668 A | 7/1996 | Mann et al. |
| 5,593,369 A | 1/1997 | Stern |
| 5,772,620 A | 6/1998 | Szlema et al. |
| 5,916,186 A * | 6/1999 | Turto ............... A61F 5/0118 602/12 |

(Continued)

OTHER PUBLICATIONS

Official Action from corresponding European Application No. 15183444.7, dated May 19, 2016.

*Primary Examiner* — Kim M Lewis
(74) *Attorney, Agent, or Firm* — Porter Wright Morris & Arthur LLP (57) ABSTRACT

A wrist-hand-finger orthosis (100, 200) comprises a splint (110, 210) comprising a supporting splint section (120, 220) extending over the MCP joints and at least a greater portion of the fingers. The supporting splint section (120, 220) has a dorsal main surface (126, 226) adapted to face the palmar side of the hand. A wrist and forearm splint section (130, 230) is connected to or integral with the supporting splint section (120, 220). Inflatable bladders (140, 240; 150, 250) are arranged on the dorsal main surface (126, 226) at a MCP portion (122, 22) and a phalanx portion (124, 224) of the supporting splint section (120, 220) to be aligned with the MCP joints of the hand and the phalanges of fingers, respectively. The orthosis (100, 200) is particularly useful for human subjects having suffered from neurological diseases or cerebrovascular accident (CVA).

18 Claims, 9 Drawing Sheets

(56) References Cited

U.S. PATENT DOCUMENTS 6,986,779 B2 * 1/2006 Begley .................. A61H 39/04
601/148
7,559,908 B2 * 7/2009 Ravikumar .......... A61B 17/135
602/13

* cited by examiner

WRIST-HAND-FINGER ORTHOSIS

TECHNICAL FIELD

The present embodiments generally relate to wrist-hand-finger orthoses, and in particular to such orthoses useful for human subjects having suffered from neurological diseases or cerebrovascular accident (CVA).

BACKGROUND

Orthoses are externally applied devices that can be used to modify or support structural and/or functional characteristics of the neuromuscular and skeletal system. Orthoses may be used in various applications to control, guide, limit or immobilize an extremity, a joint and/or a body segment of a human subject.

For instance, U.S. Pat. No. 5,772,620 relates to a hand and wrist joint orthosis designed to support the hand of a human subject in the so-called intrinsic-plus position. The hand and wrist joint orthosis is in particular intended to be used for human subjects suffering from tendovaginitis but may also be used in the case of severe distortions, after wrist joint operations and tendon operations.

The hand and wrist joint orthosis is in the form of a splint angled at positions corresponding to the wrist joint, metacarpophalangeal (MCP) joints and proximal interphalangeal (PIP) joints to support the hollow hand and permit the intrinsic-plus position. The splint is housed in a profile-sewn supporting body fixating the splint to the hand and forearm of the human subject by means of inelastic VELCRO® strip fasteners.

U.S. Pat. Nos. 5,383,827; 5,466,202 and 5,593,369 disclose an inflatable hand orthosis that promotes a functional positioning of the fingers and thumb of a human subject. The hand orthosis is in particular designed to assist in prevention and correction of hand and finger contracture and deformity in human subjects having suffered from stroke, paralysis, muscle tendon injury or nerve injury.

The inflatable hand orthosis is in the form of an inflatable bladder to be positioned between the palm and fingers. A plurality of inner seams are present on the bladder on the side opposite to the palm side for forming interconnected passages. These passages are adapted for aligning and extending the fingers and abducting the thumb.

U.S. Pat. No. 5,916,186 discloses a hand splint with a forearm support, an elongated and inelastically deformable connector and a hand piece. The connector can be adjusted to accommodate various contractures to a patient's wrist, hand or fingers.

There is, however, still a need for improvements within the technical field of wrist-hand-finger orthoses and in particular for human subjects having spasticity and/or contractures in the wrist, hand and/or digits, such as following a neurological disease or cerebrovascular accident.

SUMMARY

It is a general objective to provide an improved wrist-hand-finger orthosis.

It is a particular objective to provide a wrist-hand-finger orthosis useful for human subjects having spasticity and/or contractures in the wrist, hand and/or digits, such as following a neurological disease or CVA.

These and other objectives are met by embodiments disclosed herein.

An aspect of the embodiments relates to a wrist-hand-finger orthosis (WHFO) comprising a splint and inflatable bladders. The splint comprises a supporting splint section adapted to extend over the metacarpophalangeal (MCP) joints of the fingers of a hand of a human subject and at least a greater portion of the fingers. The supporting splint section has a dorsal main surface adapted to face a palmar side of the hand. The splint also comprises a wrist and forearm splint section integral with or connected to the supporting splint section. The wrist and forearm splint section extends from the supporting splint section to a distance corresponding to at least a portion of a forearm of the human subject. A first inflatable bladder of the WHFO is arranged on the dorsal main surface of the supporting splint section at a MCP portion of the supporting splint section to be aligned with the MCP joints of the hand. A second inflatable bladder of the WHFO is arranged on the dorsal main surface of the supporting splint section at a phalanx portion of the supporting splint section to be aligned with the phalanges of the fingers. The inflatable bladders are inflatable by introduction of a fluid within the respective interior chamber of the inflatable bladders.

The inflatable bladders on the supporting splint section constitute individually adjustable supports to the MCP joints and the phalanges of the human subject's fingers that are used together with support of the fingers on the supporting splint section and the wrist on the wrist and forearm splint section. The level of inflation of the inflatable bladders can be adjusted gradually to follow the progress of the human subject. The inflatable bladders can thereby be used to open up the hand and to provide pressure absorption and finger extension. In this way, the WHFO can be used for spasticity reduction and to prevent or stretch contractures in the fingers and wrist, such after a neurological disease or cerebrovascular accident.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present embodiments generally relate to a wrist-hand-finger orthosis (WHFO), sometimes simply referred to as hand orthosis or wrist-hand orthosis within the technical field. The WHFO of the embodiments is particular useful for human subjects having spasticity and/or contractures in the wrist, hand and/or digits. Such medical conditions, i.e. spasticity and/or contractures, may occur in subjects having suffered from a neurological disease or cerebrovascular accident (CVA), also referred to as cerebrovascular insult (CVI) or simply stroke.

The WHFO of the embodiments will then be beneficial for such human subjects by being able to reduce spasticity and prevent or stretch contractures in the digits, hand and wrist after the neurological disease or CVA.

The WHFO of the embodiments have significant advantages over prior art WHFOs by being adaptable to the subject's current disease status. Hence, the WHFO can be adapted during use to match the current spasticity and/or contracture of the subject through, among others, the use of at least two inflatable bladders in the WHFO. The amount of fluid introduced in the respective inflatable bladder and thereby the overall shape of the inflatable bladders can be selected based on the subject's particular needs and disease status.

An aspect of the embodiments relates to a WHFO comprising a splint and a first inflatable bladder and a second inflatable bladder. The splint comprises a supporting splint section adapted to extend over the metacarpophalangeal (MCP) joints of the fingers of a hand of a human subject and at least a greater portion of the fingers. The supporting splint section has a dorsal main surface adapted to face a palmar side of the hand. The splint also comprises a wrist and forearm splint section integral with or connected to the supporting splint section. The wrist and forearm splint section extends from the supporting splint section to a distance corresponding to at least a portion of a forearm of the human subject. The first inflatable bladder of the WHFO is arranged on the dorsal main surface of the supporting splint section at a MCP portion of the supporting splint section to be aligned with the MCP joints of the hand. The first inflatable bladder is inflatable by introduction of a fluid within the interior chamber of the first inflatable bladder. The second inflatable bladder of the WHFO is arranged on the dorsal main surface of the supporting splint section at a phalanx portion of the supporting splint section to be aligned with the phalanges of the fingers. The second inflatable bladder is inflatable by introduction of a fluid within an interior chamber of the second inflatable bladder.

Various embodiments of the WHFO will now be further described with reference to the drawings.

Figure 1:
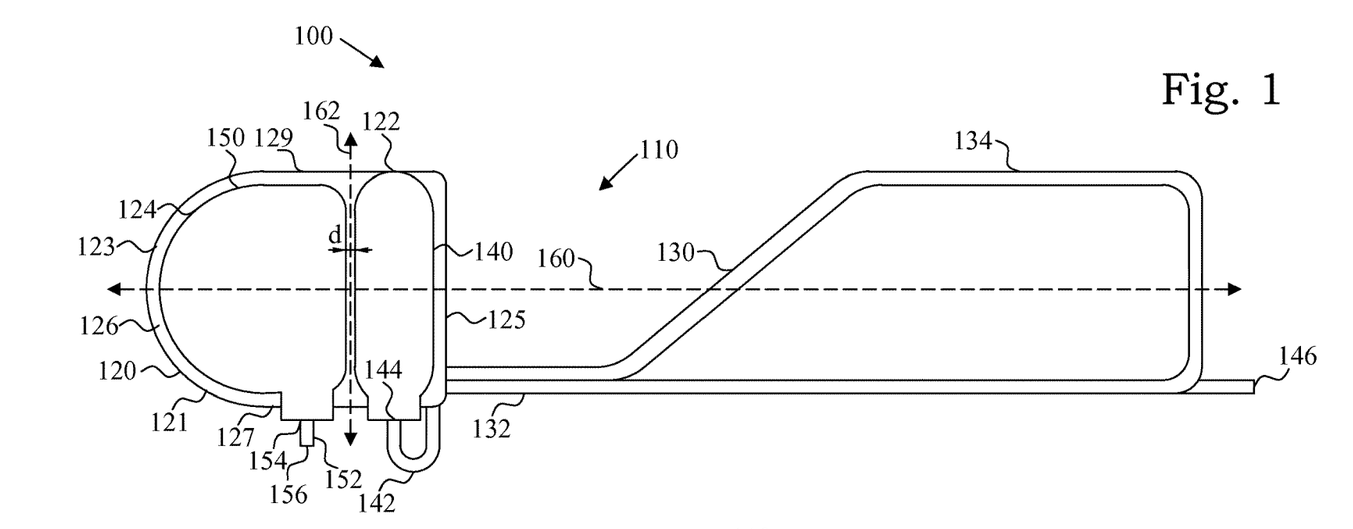
FIG. 1 schematically illustrates a WHFO according to an embodiment in a view from above.
Figure 2:
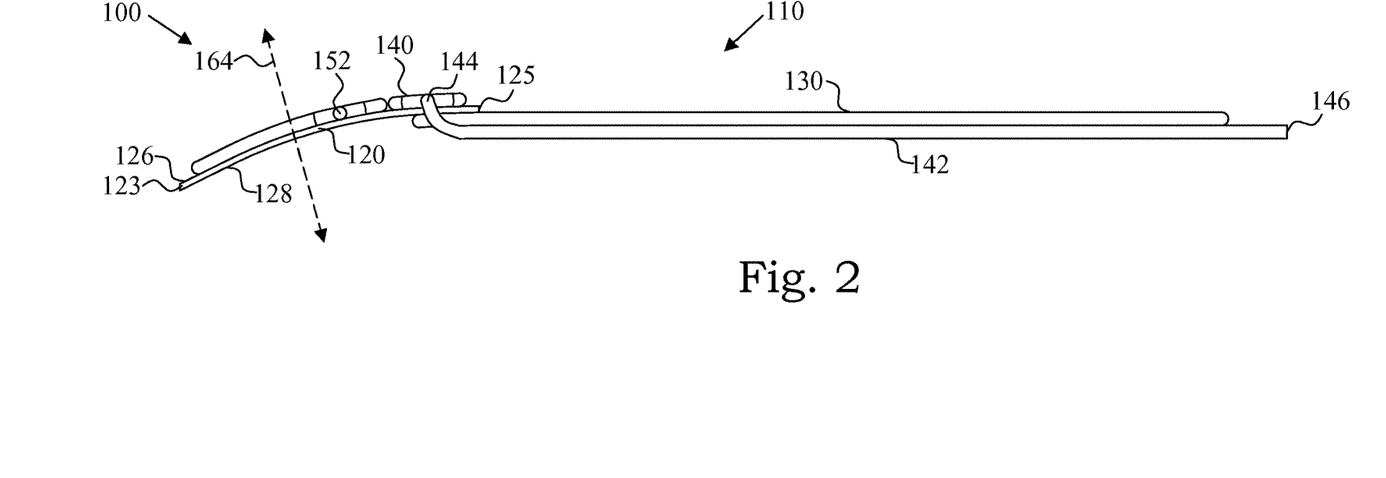
FIG. 2 schematically illustrates the WHFO in FIG. 1 in a side view.

FIG. 1 schematically illustrates a WHFO 100 according to an embodiment in a view from above with FIG. 2 illustrating the WHFO 100 in a side view. The WHFO comprises a splint 110 with the supporting splint section 120 and the wrist and forearm splint section 130. The supporting splint section 120 is constructed to extend over the MCP joints of the human subject's fingers and at least a greater portion of the fingers. The supporting splint section 120 has a dorsal main surface 126 adapted to face a palmar side of the human subject's hand, i.e. face the palm or inside of the hand, and an opposite palmar main surface 128.

The supporting splint section 120 extends over at least a greater portion of the fingers of the hand of a human subject. This corresponds, in an embodiment, to at least the MCP joints of the fingers and preferably also at least a portion of the phalanges of the fingers. In an embodiment, the supporting splint section 120 extends over the metacarpals, or at least a distal portion thereof, and at least the proximal phalanges of the fingers. More preferably, the supporting splint section 120 extends over the metacarpals, or at least a distal portion thereof, and at least the proximal phalanges and intermediate phalanges of the fingers. In an embodiment, the supporting splinting section 120 may also extend over the distal phalanges of the fingers.

The fingers that the supporting splint section 120 extends over preferably include the index finger (digit II), the middle finger (digit III), the ring finger (digit IV) and the little finger or pinky (digit V). The human hand, normally, also includes the thumb (digit I), resulting in five digits.

In the illustrated embodiment, the supporting splint section 120 is in the form of a sheet 121 having a distal rounded end 123 and a proximal end 125. The proximal end 125 extends substantially along a radial-to-ulnar or transversal axis 162 over the palm of the human subject's hand. This radial-to-ulnar axis 162 extends between an ulnar side 127 of the supporting splint section 120 and a radial side 129 of the supporting splint section 120. The wrist and forearm splint section 130 is then preferably connected to the supporting splint section 120 and extends from the proximal end 125 of the supporting splint section 120.

The supporting splint section 120 is preferably deformable to adapt the shape of the sheet 121 to a suitable position of the human subject's hand and fingers. Thus, the sheet 121 could be shaped from a substantially planar sheet 121 to be bent or curved to match contracted fingers. In a general embodiment, the supporting splint section 120 is deformable to support the hand and the fingers in a functional position.

Functional position as used herein refers to a resting position of the hand and the fingers. In such a resting position, the MCP joints are typically in 40° to 60° flexion of the fingers towards the palm (palmar flexion) and the proximal interphalangeal (PIP) joints from a slight flexion up to about 60° flexion of the fingers towards the palm (palmar flexion).

The wrist and forearm splint section 130 comprises, in the illustrated embodiment, a forearm portion 134 to be aligned with human subject's forearm and a wrist portion 132 interconnecting the forearm portion 134 and the supporting splint section 120. In an embodiment, the forearm portion 134 has a wire-based open frame structure as shown in FIG. 1.

The wrist and forearm splint section 130 could then be constructed as a wire extending longitudinally, i.e. along a distal-to-proximal axis 160, and then turning back to form an open frame structure or loop. The wire preferably extends back to the supporting splint section 120, where the two ends of the wire are attached to the supporting splint section 120, such as the palmar main surface 128 or the proximal end 125 of the supporting splint section 120.

In such a case, the longitudinal portions of the wire extending substantially along the distal-to-proximal axis 160 will run along a portion of the length of the human subject's forearm. Correspondingly, the transversal portions extending substantially along or angled (diagonally) relative to the radial-to-ulnar axis 162 extend over the underside or caudal side of the forearm.

The wrist portion 132 preferably not only interconnects the forearm portion 134 of the wrist and forearm splint section 130 and the supporting splint section 120 but is preferably deformable in at least a portion adapted to be aligned with the wrist joint of the human subject's hand. In such a case, the angle between the forearm portion 134 and the supporting splint section 120 can be adapted to a suitable angle of the human subject's wrist.

Generally, the wrist portion 132 is preferably adapted to support the wrist in 0° to 20° extension relative to the back of the hand (dorsal extension).

The supporting splint section 120 has a MCP portion 122, which is adapted to be aligned with the MCP joints of the human subject's hand. The first inflatable bladder 140 of the WHFO 100 is arranged on the dorsal main surface 126 at the MCP portion 122.

The first inflatable bladder 140 is inflatable by introduction of a fluid within an interior chamber of the first inflatable bladder 140. The fluid could, for instance, be a gas, including a gas mixture, or a liquid. The fluid is preferably air. In a deflated state, the first inflatable bladder 140 is positioned substantially flat on the dorsal main surface 126 at the MCP portion 122. However, once the fluid, such as air, is being introduced, typically pumped, into the interior chamber of the first inflatable bladder 140, the first inflatable bladder 140 starts to expand and extend from the dorsal main surface 126.

The first inflatable bladder 140 is advantageously attached to the dorsal main surface 126 at the MCP portion 122. Various means for attaching the first inflatable bladder 140 to the dorsal main surface 126 are possible, for instance gluing, welding, etc. depending on the particular materials of the first inflatable bladder 140 and the supporting splint section 120.

The introduction of fluid into the interior chamber of the first inflatable bladder 140 causes an upper or dorsal portion of the first inflatable bladder 140 to rise from the dorsal main surface 126, while the lower or palmar portion of the first inflatable bladder 140 is preferably still attached to the dorsal main surface 126.

The WHFO 100 preferably also comprises a first fluid tube 142 having a first end 144 in fluid connection with the inner chamber of the first inflatable bladder 140 and a second end 146 connectable to a pump adapted to introduce the fluid into the inner chamber of the first inflatable bladder 140 through the first fluid tube 142.

The first fluid tube 142 thereby functions as a connection between the first inflatable bladder 140 and a pump to be used for introducing fluid, such as air, into the inner chamber of the first inflatable bladder 140. The first fluid tube 142 is preferably in the form of tube with an inner channel through which the fluid can be pumped from the second end 146 to the first end 144 and into the first inflatable bladder 140.

FIG. 1 illustrates an embodiment of arranging the first fluid tube 142 relative to the splint 110. In this embodiment, the first fluid tube 142 extends along at least a portion of a distal-to-proximal length of the wrist and forearm splint section 130.

Thus, the first fluid tube 142 preferably extends longitudinally along the distal-to-proximal axis 160 to end somewhere along the distal-to-proximal length of the wrist and forearm splint section 130 or indeed protrudes past the proximal end of the wrist and forearm splint section 130 as shown in the figure. In such a case, the first fluid tube 142 could be bent around one of the ulnar side 127 and the radial side 129 of the supporting splint section 120 to the palmar main surface 128. The first fluid tube 142 then extends along the wire of the wire-based wrist and forearm splint section 130 to the proximal end thereof. This is more clearly seen in FIG. 2, which illustrates the WHFO 100 of FIG. 1 shown in a side view.

It is generally preferred if the second end 146 of the first fluid tube 142 ends substantially at or protrudes slightly past the proximal end of the wrist and forearm splint section 130. At this position the second end 146 is easily accessible and can be connected to the pump in order to inflate or deflate the first inflatable bladder 140.

In alternative embodiments, the second end 146 is aligned with any portion of the wrist and forearm splint section 130 from its distal end at the supporting splint section 120 up to its proximal end.

In an alternative embodiment, the first fluid tube 142 does not extend along at least a portion of the length of the wrist and forearm splint section 130. In clear contrast, the first fluid tube 142 extends towards the ulnar side 127 or the radial side 129 of the supporting splint section 120. The length of the first fluid tube 142 can then be kept quite short so that it basically corresponds to a connection port for the pump.

A further variant is to have the first fluid tube 142 bent around the ulnar side 127 or the radial side 129 of the supporting splint section 120 and extending along at least a portion of the palmar main surface 128 of the supporting splint section 120. In this embodiment, the second end 146 of the first fluid tube 142 thereby ends somewhere along the palmar main surface 128.

The supporting splint section 120 of the WHFO 100 and its attached or connected first inflatable bladder 140 will, by inflating the first inflatable bladder 140, provide an individually adjustable support to the MCP joints of the human subject's fingers together with support of the fingers on the supporting splint section 120 and the wrist on the wrist and forearm splint section 130. The pump that is connectable to the first inflatable tube 146 is used to introduce fluid, such as air, into the first inflatable bladder 140 to a suitable level depending on the subject's needs and medical condition. The level of inflation of the first inflatable bladder 140 can be adjusted gradually to follow the progress of the human subject. The first inflatable bladder 140 can thereby be used to open up the hand and to provide pressure absorption and finger extension.

In this way, the WHFO 100 can be used for reduction of spasticity and/or to prevent or stretch contractures in the fingers and wrist, such after a neurological disease or CVA.

The second inflatable bladder 150 is arranged on the dorsal main surface 126 of the supporting splint section 120 at a phalanx portion 124 of the supporting splint section 120. This phalanx portion 124 is to be aligned with the phalanges of the human subject's fingers. The second inflatable bladder 150 is inflatable by introduction of a fluid within an interior chamber of the second inflatable bladder 150.

In a particular embodiment, the second inflatable bladder 150 is arranged on the dorsal main surface 126 at the phalanx portion 124 to be aligned with the PIP joints and the distal interphalangeal (DIP) joints of the human subject's fingers.

Thus, while the first inflatable bladder 140 is arranged on the supporting splint section 120 to support the MCP joints of the subject's fingers, the second inflatable bladder 150 is correspondingly arranged on the supporting splint section 120 to support the PIP and DIP joints of the fingers. In such an embodiment, the second inflatable bladder 150 preferably supports the proximal phalanges, the intermediate phalanges and the distal phalanges of the human subject's fingers.

The two inflatable bladders 140, 150 may be arranged on the supporting splint section 120 with a distance (d) therebetween. This distance may range from a quite low value, such as one or a few mm, up to several mm. Generally, the distance d is preferably within the interval of 1-20 mm, more preferably within 1-10 mm, such as at a distance of 1 mm, 2 mm, 3 mm, 4 mm, 5 mm, 6 mm, 7 mm, 8 15 mm, 9 mm or 10 mm. It is also possible to have a substantially zero distance between the two inflatable bladders 140, 150 in a deflated state with the two inflatable bladders 140, 150 at least partly contacting each other.

The first inflatable bladder 140 is preferably elongated along the radial-to-ulnar axis 162 and has a general "sausage-like" shape when inflated. This shape of the first inflatable bladder 140 is effectively adapted to and supports the MCP joints of the fingers. The second inflatable bladder 150 generally has a larger extension along the dorsal main surface 126 as compared to the first inflatable bladder 140. The reason being that the second inflatable bladder 150 is preferably shaped to be adapted to and support the PIP and DIP joints of the fingers.

The WHFO 100 preferably comprises a second fluid tube 152 having a first end 154 in fluid connection with the inner chamber of the second inflatable bladder 150 and a second end 156 connectable to a pump adapted to introduce the fluid into the inner chamber of the second inflatable bladder 150 through the second fluid tube 152.

The second fluid tube 152 thereby has the same function as the first fluid tube 142 to guide fluid, such as air, from a pump connected to the second end 146, 156 into the inner chamber of the inflatable bladder 140, 150. The fluid tubes 142, 152 may likewise be used when deflating the inflatable bladders 140, 150, optionally using the pump.

The second fluid tube 152 could be designed and arranged in substantially the same way as the first fluid tube 142.

Thus, in a first embodiment, the second fluid tube 152 extends towards the ulnar side 127 or the radial side 129 of the supporting splint section 120 as shown in FIGS. 1 and 2.

Figure 3:
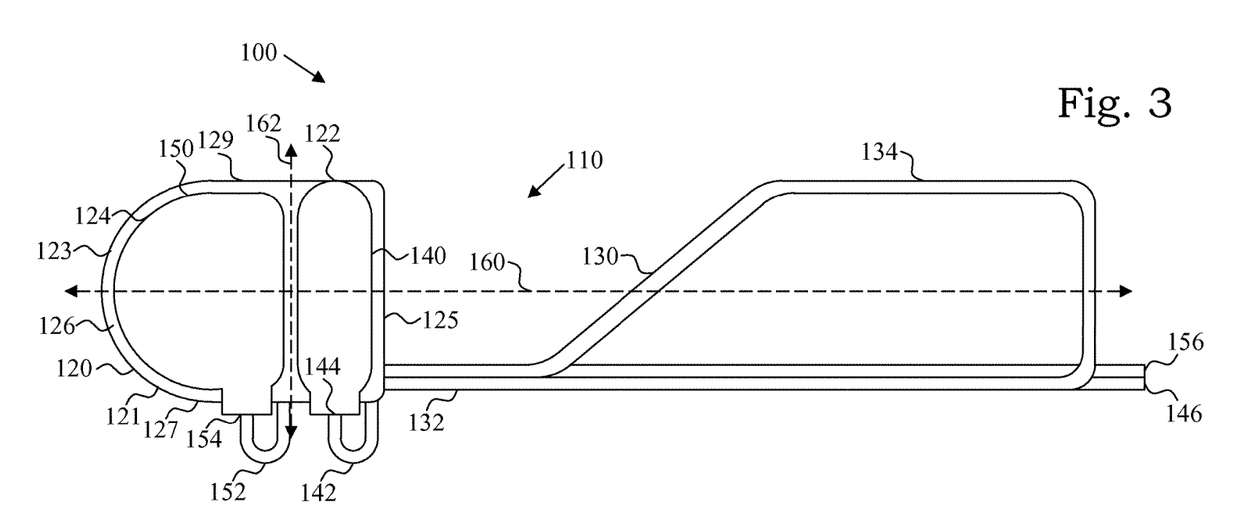
FIG. 3 schematically illustrates a WHFO according to another embodiment in a view from above.

In a second embodiment, the second fluid 152 extends along at least a portion of a distal-to-proximal length or axis 160 of the wrist and forearm splint section 130 as shown in FIG. 3. If the first fluid tube 142 also extends along the distal-to-proximal axis 160 the two fluid tubes 142, 152 could end substantially at the same position relative to the proximal end of the wrist and forearm section 130 as shown in FIG. 3. In such a case, the two fluid tubes 142, 152 may have different colors or markings, different cross-sectional shapes, etc. to facilitate identifying which of the fluid tubes 142, 152 that is connected to the first fluid bladder 140 and which is connected to the second fluid bladder 150. Alternatively, the second ends 146, 156 of the two fluid tubes 142, 152 could be kept separated a distance apart along the distal-to-proximal axis 160 and/or along the radial-to-ulnar axis 162 in order reduce the risk of mixing up the two fluid tubes 142, 152.

Figure 4:
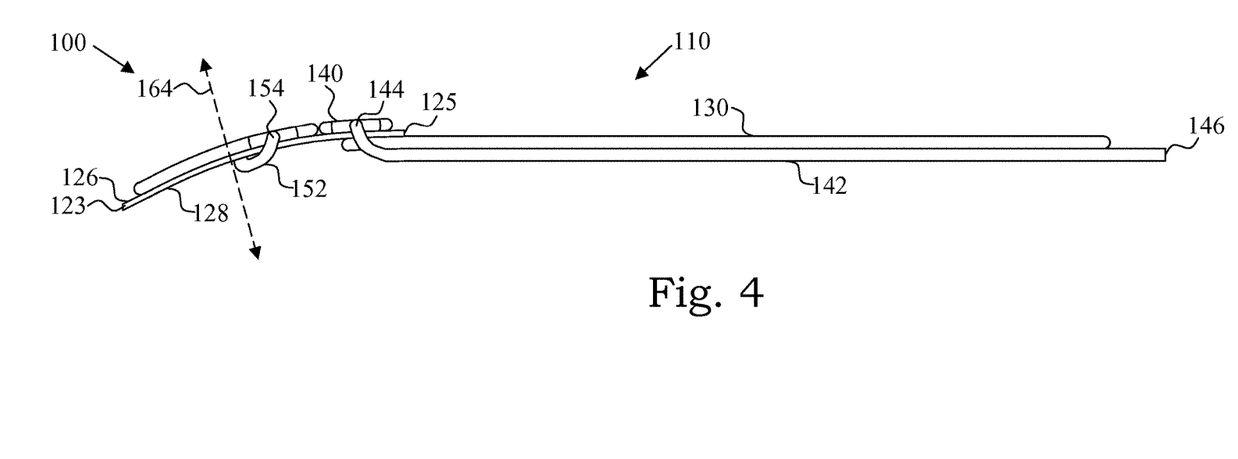
FIG. 4 schematically illustrates a WHFO according to a further embodiment in a side view.

In a third embodiment, the second fluid tube 152 is bent around the ulnar side 127 or the radial side 129 of the supporting splint section 120 and extends along at least a portion of the palmar main surface 128 of the supporting splint section 120, see FIG. 4.

In the embodiments shown in FIGS. 1-4, the first fluid tube 142 extends along at least a portion of the distal-to-proximal length of the wrist and forearm splint section 130. The embodiments are, however, not limited thereto. Hence, the embodiments encompass a WHFO 100 with both the first and fluid tubes 142, 152 extending along at least a portion of the distal-to-proximal length of the wrist and forearm splint section 130. The embodiments also encompass a WHFO 100 with both the first and second fluid tubes 142, 152 extending towards the ulnar side 127 or the radial side 129 of the supporting splint section 120 or with one of the first and second tubes 142, 154 extending towards the ulnar side 127 and the other extending towards the radial side 129. The embodiments further encompass a WHFO 100 with both the first and second fluid tubes 142, 152 extending along at least a portion of the palmar main surface 128 of the supporting splint section 120. Other embodiments encompass a WHFO 100 with one of the first and second fluid tubes 142, 152 extending along at least a portion of the distal-to-proximal length of the wrist and forearm splint section 130 and the other extending towards the ulnar side 127 or the radial side 129 of the supporting splint section 120. Further embodiments encompass a WHFO 100 with one of the first and second fluid tubes 142, 152 extending along at least a portion of the distal-to-proximal length of the wrist and forearm splint section 130 and the other extending along at least a portion of the palmar main surface 128 of the supporting splint section 120. Yet another embodiment encompass a WHFO 100 with one of the first and second tubes 142, 152 extending towards the ulnar side 127 or the radial side 129 of the supporting splint section 120 and the other extending along at least a portion of the palmar main surface 128 of the supporting splint section 120.

The second ends 146, 156 of the first and second fluid tubes 142, 152 preferably comprise a valve that is opened when the pump is connected to the second end 146, 156 and presses fluid, such as air, into the fluid tube 142, 152 through the second end 146, 156. Correspondingly, when the fluid flow into the fluid tube 142, 152 stops the valve preferably closes the fluid channel in the fluid tube 142, 152 to thereby prevent fluid from escaping from the inflatable bladder 140, 150. In a particular embodiment, the pump or another equipment can also be used to deflate the inflatable bladder 140, 150 by sucking or draining fluid out from the inflatable bladder 140, 150 through the fluid tube 142, 156 and the valve at the second end 146, 156.

In a simpler embodiment, a plug is inserted into the second end 146, 156 of the fluid tube 142, 152 following inflating the inflatable bladder 140, 150 by the pump to prevent the fluid from escaping. When the inflatable bladder 140, 150 is to be deflated, the plug is simply removed from the second end 146, 156 allowing fluid to escape from the inflatable bladder 140, 150. This embodiment provides an easier construction relaxing the need for a valve at the second end 146, 156. However, it generally leads to less control of the inflation level of the inflatable bladder 140, 150.

Figure 5:
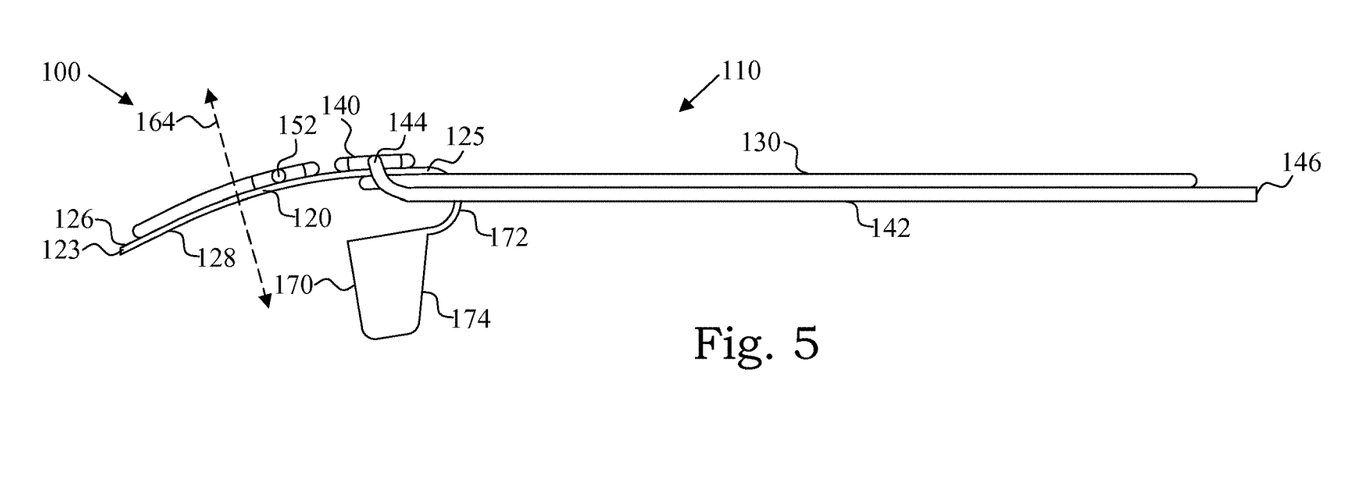
FIG. 5 schematically illustrates a WHFO according to yet another embodiment in a side view.
Figure 6:
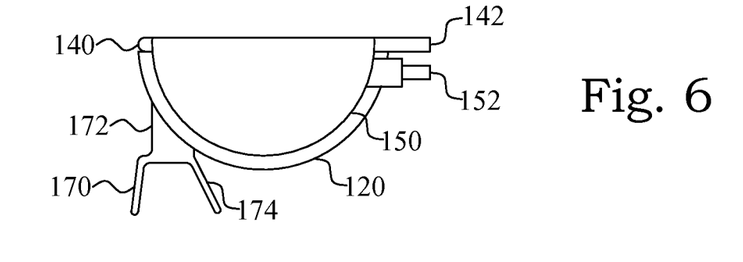
FIG. 6 schematically illustrates the WHFO in FIG. 5 in a front view.
Figure 7:
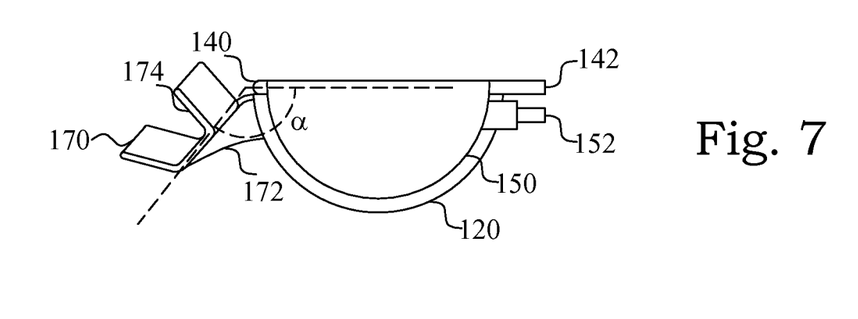
FIG. 7 schematically illustrates a WHFO according to yet another embodiment in a front view.

The splint 110 of the WHFO 100 optionally, but preferably, comprises a thumb support 170, see FIGS. 5-7. The thumb support 170 is connected to or integral with the supporting splint section 120.

In such a case, the splint 110 provides support not only to the fingers of the human subject's hand resting along the supporting splint section 120 with the first inflatable bladder 140 and the second inflatable bladder 150 but also for the thumb, i.e. all digits of the hand.

FIGS. 5 and 6 illustrate an embodiment of the thumb support 170 as seen in a side view and a front view, respectively. The thumb support 170 preferably comprises a phalanx portion 174 adapted to support the phalanges of the thumb. A connecting portion 172 of the thumb support 170 interconnects the phalanx portion 174 to the supporting splint section 120. This connecting portion 172 may additionally be adapted to support the metacarpal of the thumb.

The phalanx portion 174 and the connecting portion 172 are preferably made as a single unitary unit, such as a pre-shaped sheet that is bent to support the thumb. Alternatively, the phalanx portion 174 and the connecting portion 172 could be manufactured as at least two different units that are attached together forming the thumb support 170.

In an embodiment, the phalanx portion 174 could comprise a supporting surface adapted to support the phalanges of the thumb and two wall sections extending from the supporting surface to limit the thumb from sliding away from the supporting surface. The connecting portion 172 could be in the form of a bent sheet that extends from or is connected to the phalanx portion 174 and attaches the phalanx portion 174 to the supporting splint section 120, preferably at the palmar main surface 128 or the dorsal main surface 126 of the supporting splint section 120. The bend in the connecting portion 172 is preferably adapted to the MCP joint and PIP joint of the thumb.

The phalanx portion 174 is preferably separated with a distance along a dorsoplamar axis 164 from the palmar main surface 128 of the supporting splint section 120. In such a position, the thumb support 170 is adapted to support the thumb in the so-called first projection.

In the embodiment shown in FIGS. 5 and 6 with the thumb kept in the first projection the thumb support 170 substantially supports the thumb parallel with but at a distance from the palmar main surface 128 of the supporting splint section 120.

FIG. 7 illustrates another embodiment of arranging the thumb support 170 relative to the supporting splint section 120. This embodiment is adapted to support the thumb in the so-called volar abducted position. In such a case, the phalanx portion 174 is angled relative to the palmar main surface 128 of the supporting splint section 120 with an angle (α) that is within an interval of 120° and 150°. Hence, at this position the thumb is supported extending slightly below the dorsal main surface 126 and at a distance from the radial side 129 of the supporting splint section 120.

The splint 110 of the WHFO 100 as illustrated in FIGS. 1-7 is preferably manufactured from a metal material, including a metal alloy material. Suitable, but non-limiting examples of such materials include, iron alloys, aluminum and aluminum alloys, e.g. malleable aluminum or aluminum alloys.

The metal material of the splint 110 is preferably deformable at least in the supporting splint section 120 and the wrist portion 132 of the wrist and forearm splint section 130. Hence, the metal material is preferably not brittle and can be bent slightly to form a curvature of the supporting splint section 120 and a bend at the wrist portion 132 that are adapted to the particular human subject.

Although metal materials may be suitable for manufacturing the splint 110 other materials could alternatively be used, such as plastics and in particular low temperature thermoplastics, e.g. such low temperature thermoplastics that are heated in hot water at, for instance, 75 to 85° C. or using at heat gun.

Figure 8:
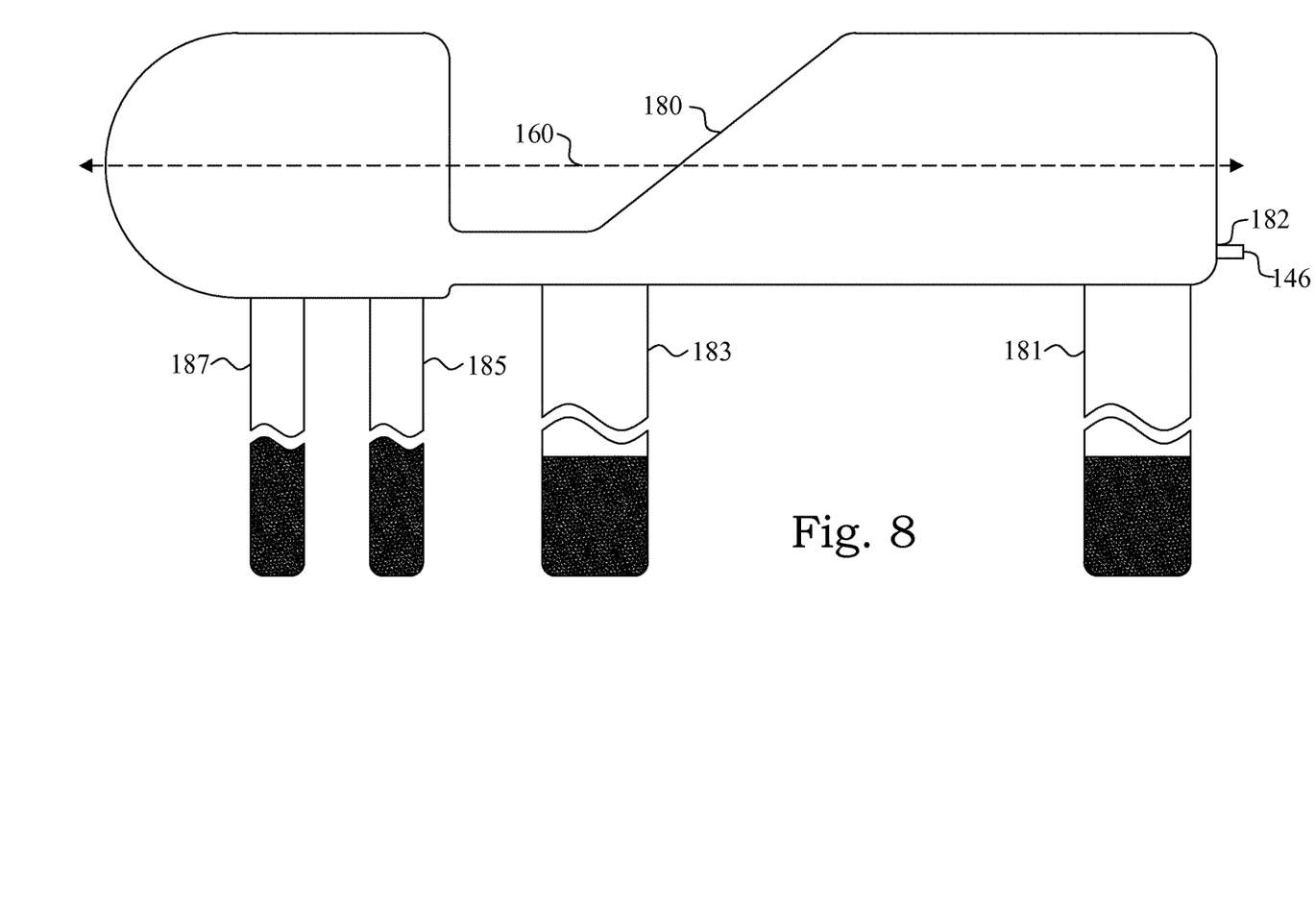
FIG. 8 schematically illustrates a textile dress according to an embodiment.
Figure 9:
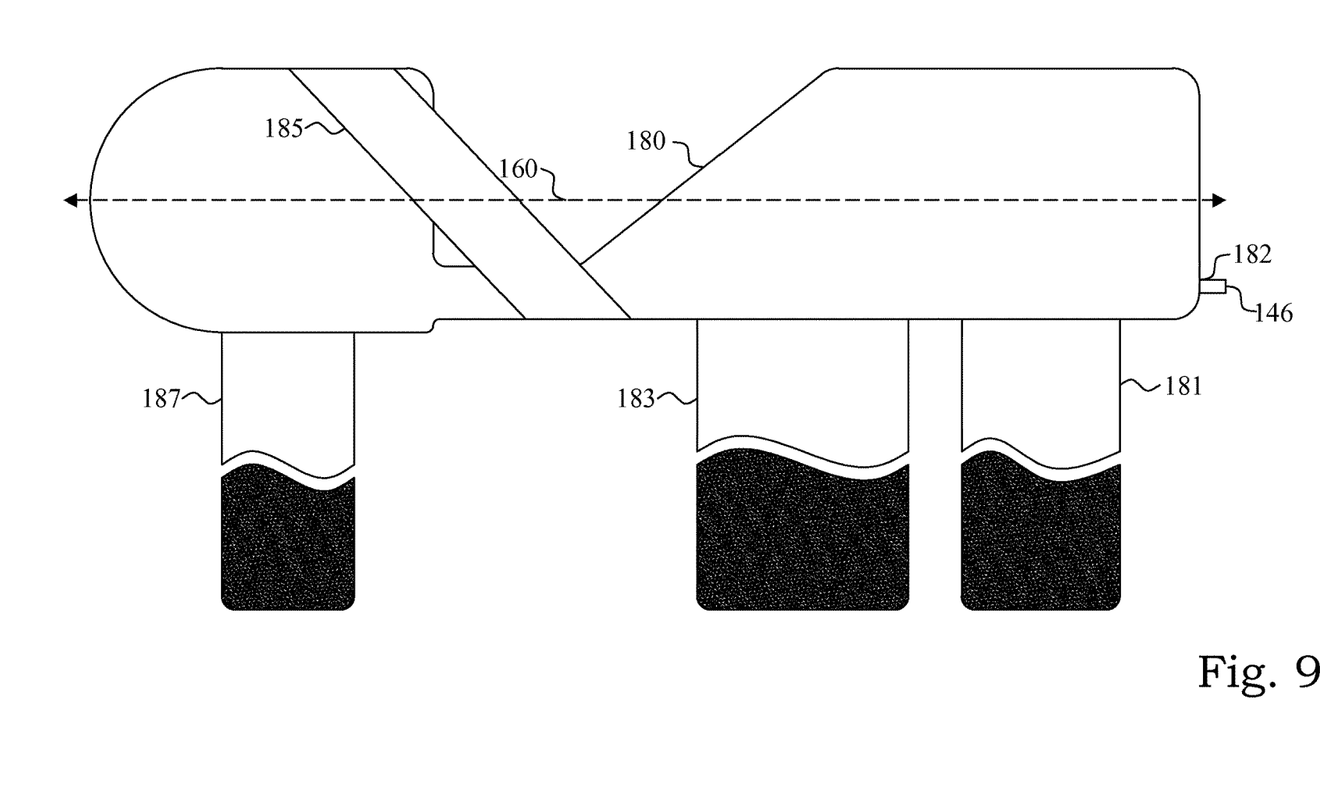
FIG. 9 schematically illustrates a textile dress according to another embodiment.

The WHFO 100 as shown in FIGS. 1-7 preferably comprises a textile dress 180, also referred as cloth dress, see FIGS. 8 and 9. The textile dress 180 has an interior chamber adapted to house the splint 110 and the first inflatable bladder 140 and the second inflatable bladder 150. The textile dress 180 comprises an opening 182 providing access to the first fluid tube 142. The opening 182 in the textile dress 180 also provides access to the second fluid tube 152 or the textile dress 180 comprises a second opening providing access to the second fluid tube 152.

The textile dress 180 comprises multiple closing straps 181, 183, 185, 187 arranged along a distal-to-proximal axis 160 of the textile dress 180. In such a case, at least one closing strap 185, 187 is arranged at a portion of the textile dress 180 aligned with the supporting splint section 120 when the splint 110 is housed within the interior chamber of the textile dress 180. Furthermore, at least one closing strap 181, 183 is arranged at a portion of the textile dress 180 aligned with the wrist and forearm splint section 130 when the splint 110 is housed within the interior chamber of the textile dress 180. The multiple closing straps 181, 183, 185, 187 are arranged to secure the WHFO 100 to the hand and forearm of the human subject.

The textile dress 180, thus, has dual functions for the WHFO 100. Firstly, it secures the WHFO 100 to the hand and forearm of the human subject using the closing straps or bands 181, 183, 185, 187 that are wrapped around the hand and the forearm. The closing straps 181, 813, 185, 187 are preferably secured at the textile dress 180 by means of hook and loop fasteners, such as VELCRO® fasteners. In such a case, at least a portion of the closing straps 181, 183, 185, 187 comprises hook or loop material as schematically shown in FIGS. 8 and 9. The hook or loop material can then mate with loop or hook material provided on the textile dress 180 or on the opposite side of the closing straps 181, 183, 185, 187. The mating between the loop and hook material is non-permanent implying that the closing straps 181, 183, 185, 187 may be opened and closed when removing and attaching the WHFO 100 to a subject, respectively.

Secondly, the textile dress 180 constitutes a soft surface facing the skin of the hand and forearm. The textile dress 180 could thereby provide pressure absorption to make the WHFO 100 comfortable to wear.

Various textile materials can be used, including filled textile materials.

FIG. 8 illustrates a textile dress 180 having two closing straps 185, 187 aligned with the supporting splint section 120, one closing strap 181 aligned with the forearm portion 134 of the wrist and forearm splint section 130 and one closing strip 183 aligned with the wrist portion 132 of the wrist and forearm splint section 130. This should merely be seen as an illustrative example of an arrangement of closing straps 181, 183, 185, 187 in the textile dress 180.

FIG. 9 illustrates another arrangement of closing straps 181, 183, 185, 187. This embodiment of textile dress 180 is in particular suitable for human subjects having intensive spasticity, where there could be risk for the hand slipping relative to WHFO 100 even when the closing straps 181, 183, 185, 187 secure the WHFO 100 to the hand and forearm. This potential slipping problem is solved by the textile dress 180 of FIG. 9. This embodiment comprises a wider closing strap 183 aligned with the wrist and forearm splint section 130 when the splint 110 is housed within the interior chamber of the textile dress 180. In addition, a closing strap 185 runs diagonally from the ulnar side or the radial side of the textile dress 180 to the radial side or the ulnar side of the textile dress 180. FIG. 9 illustrates this closing strap 185 in a closed state showing that the closing strap 185 will rest on and run across that back of the hand. This will effectively prevent the hand and forearm of the human subject from slipping relative to the WHFO 100 even if the subject suffers from extensive spasticity. The diagonal closing strap 185 together with the thicker closing strap 183 locks the hand and forearm to the WHFO 100.

In an embodiment, the closing strap 185 preferably runs from a portion of the textile dress 180 aligned with the wrist and forearm splint section 130 to a portion of the textile dress 180 aligned with the supporting splint section 120 as shown in FIG. 9.

Figure 10:
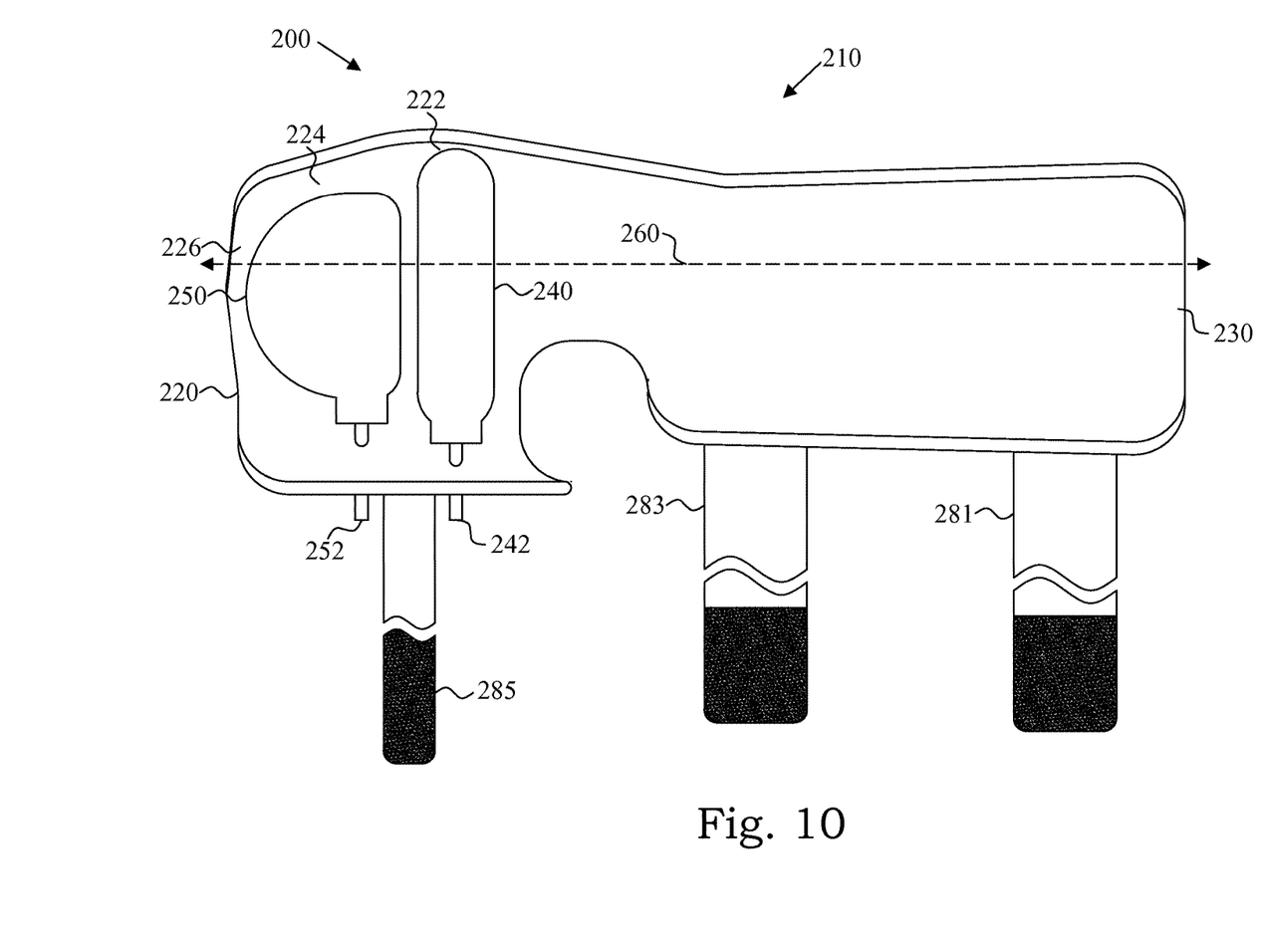
FIG. 10 schematically illustrates a WHFO according a further embodiment in a view from above.

FIG. 10 schematically illustrates another embodiment of a WHFO 200 comprising a splint 210 that is made as a unitary structure with the wrist and forearm splint section 230 integral with the supporting splint section 220. The WHFO 200 preferably also comprises multiple closing straps 281, 283, 285 arranged along the distal-to-proximal axis 260 of the splint 200 with at least one closing strap 285 arranged at the supporting splint section 220 and at least one closing strap 281, 283 arranged at the wrist and forearm splint section 230. The multiple closing straps 281, 283, 285 are arranged to secure the WHFO 200 to the hand and forearm of a human subject.

The dorsal main surface 226 of the supporting splint section 220 comprises the MCP portion 222 at which the first inflatable bladder 240 is arranged and the phalanx portion 224 at which the second inflatable bladder 250 is arranged. The figure also shows the first and second fluid tubes 242, 252. In an embodiment, the fluid tubes 242, 252 run through an opening (one common opening or two separate openings) in the radial or ulnar side of the WHFO 200.

The splint 210 could be made of a metal material as previously described herein but is advantageously made of plastics, such as a thermoplastic. In an embodiment, the splint 200 could be made of a thermoforming material, which makes it easy to reshape and adjust the splint 210 by heat, for instance using hot water or heat gun, such as low temperature thermoplastics that may be heated in hot water, for instance at 75 to 85° C., or by using a heat gun.

Although not shown in the figure, the splint 210 may comprise perforations to provide ventilation through the splint 210.

The splint 210 may also comprise a thumb support as previously described herein to support the thumb of the hand. The thumb support is preferably an integral part of the splint 210.

Figure 11:
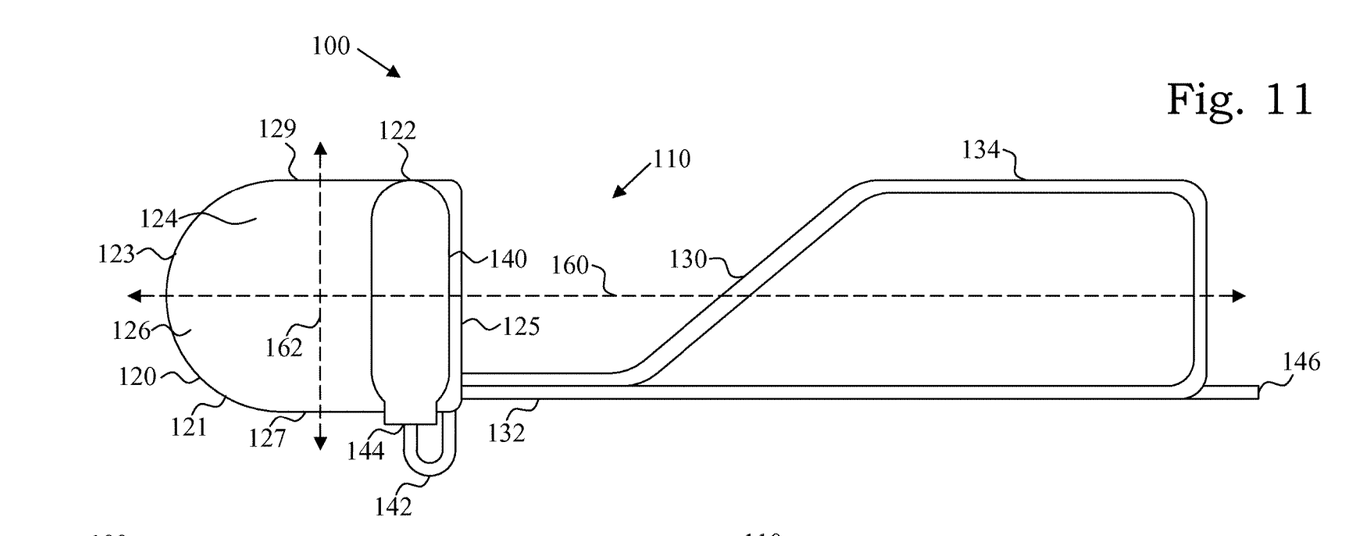
FIG. 11 schematically illustrates a WHFO with a single inflatable bladder in a view from above.
Figure 12:
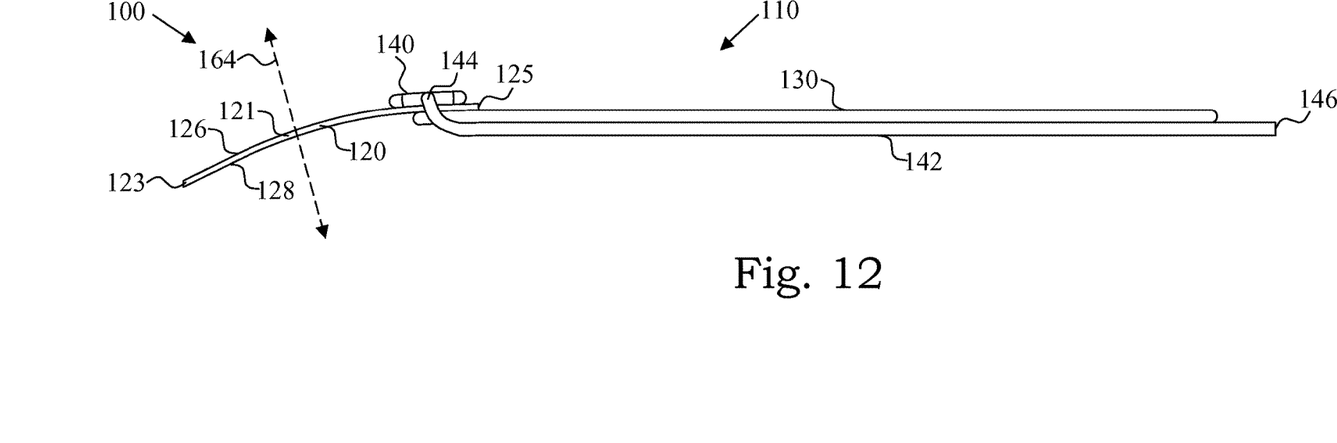
FIG. 12 schematically illustrates the WHFO in FIG. 11 in a side view.

With reference to FIGS. 11 and 12, another aspect of the embodiments relates to a WHFO 100 comprising a splint 110 comprising a supporting splint section 120 adapted to extend over the MCP joints of the fingers of a hand of a human subject and at least a greater portion of the fingers. The supporting splint section 120 has a dorsal main surface 126 adapted to face a palmar side of the hand. The splint 110 also comprises a wrist and forearm splint section 130 integral with or connected to the supporting splint section 120. The wrist and forearm splint section 130 extends from the supporting splint section 120 to a distance corresponding to at least a portion of a forearm of the human subject. The WHFO 100 also comprises, in this aspect, an inflatable bladder 140 arranged on the dorsal main surface 126 of the supporting splint section 120 at a MCP portion 122 of the supporting splint section 120 to be aligned with the MCP joints of the hand. The inflatable bladder 140 is inflatable by introduction of a fluid within an interior chamber of the inflatable bladder 140.

Figure 13:
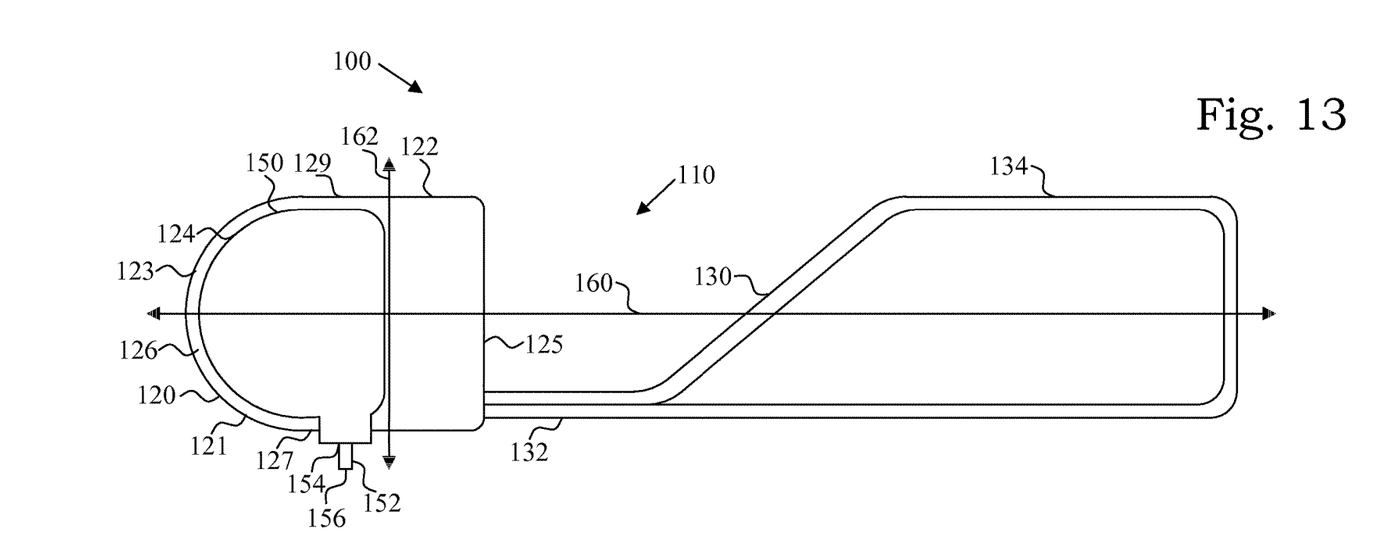
FIG. 13 schematically illustrates another WHFO with a single inflatable bladder in a view from above.
Figure 14:
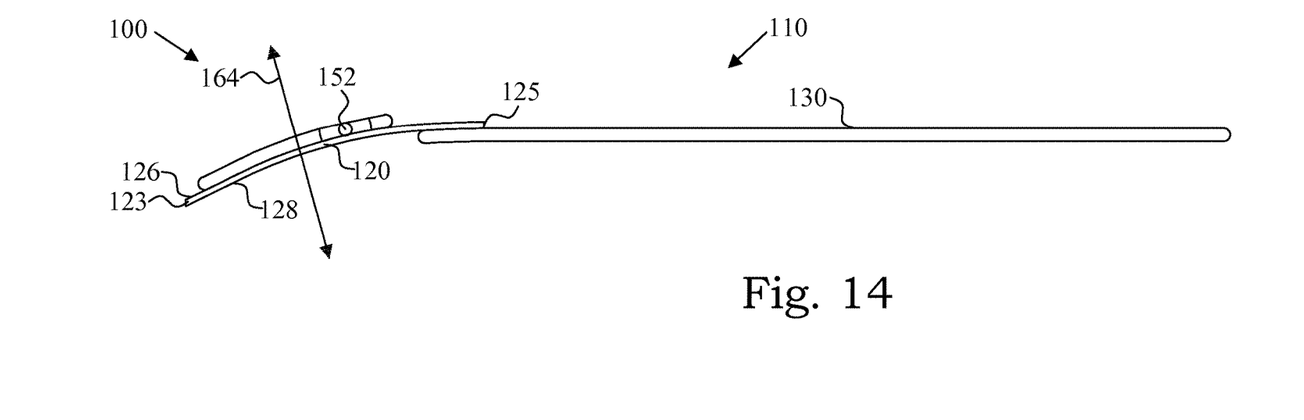
FIG. 14 schematically illustrates the WHFO in FIG. 13 in a side view.

With reference to FIGS. 13 and 14, a further aspect of the embodiments relates to a WHFO 100 comprising a splint 110 comprising a supporting splint section 120 adapted to extend over the MCP joints of the fingers of a hand of a human subject and at least a greater portion of the fingers. The supporting splint section 120 has a dorsal main surface 126 adapted to face a palmar side of the hand. The splint 110 also comprises a wrist and forearm splint section 130 integral with or connected to the supporting splint section 120. The wrist and forearm splint section 130 extends from the supporting splint section 120 to a distance corresponding to at least a portion of a forearm of the human subject. The WHFO 100 also comprises, in this aspect, an inflatable bladder 150 arranged on the dorsal main surface 126 of the supporting splint section 100 at a phalanx portion 124 of the supporting splint section 120 to be aligned with phalanges of the fingers. The inflatable bladder 150 is inflatable by introduction of a fluid within an interior chamber of the inflatable bladder 150.

These two additionally aspects thereby defines a respective WHFO 100 comprising at least one inflatable bladder 140, 150 corresponding the inflatable bladder denoted the first inflatable bladder 140 herein or the inflatable bladder denoted the second inflatable bladder 150 herein. Hence, the WHFO 100 does not necessary need to have two inflatable bladders in these two additionally aspects.

The various embodiments as disclosed herein with regard to, for instance, the design of the supporting splint section, the writ and forearm splint section, the optional fluid tubes, the optional thumb support, the optional textile dress also apply the WHFO according to these additional aspects.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A wrist-hand-finger orthosis comprising:
 a splint comprising:
  a supporting splint section adapted to extend over the metacarpophalangeal, MCP, joints of the fingers of a hand of a human subject and at least a greater portion of said fingers, said supporting splint section having a dorsal main surface adapted to face a palmar side of said hand, wherein said supporting splint section is in the form of a planar sheet having a distal rounded end and a proximal end extending substantially along a radial-to-ulnar axis over a palm of said hand, wherein said planar sheet is bent in a single arc extending from said proximal end to said distal rounded end, with said arc presenting a convex surface for supporting said hand; and
  a wrist and forearm splint section integral with or connected to said supporting splint section, said wrist and forearm splint section extending from said proximal end of said supporting splint section to a distance corresponding to at least a portion of a forearm of said human subject;
 a first inflatable bladder arranged on said dorsal main surface of said supporting splint section at a MCP portion of said supporting splint section to be aligned with said MCP joints of said hand, said first inflatable bladder being inflatable by introduction of a fluid within an interior chamber of said first inflatable bladder; and
 a second inflatable bladder arranged on said dorsal main surface of said supporting splint section at a phalanx portion of said supporting splint section to be aligned with the phalanges of said fingers, said second inflatable bladder being inflatable by introduction of a fluid within an interior chamber of said second inflatable bladder.

2. The wrist-hand-finger orthosis according to claim 1, further comprising a first fluid tube having a first end in fluid connection with said inner chamber of said first inflatable bladder and a second end connectable to a pump adapted to introduce said fluid into said inner chamber of said first inflatable bladder though said first fluid tube, said first fluid tube extending along at least a portion of a distal-to-proximal length of said wrist and forearm splint section.

3. The wrist-hand-finger orthosis according to claim 1, further comprising a first fluid tube having a first end in fluid connection with said inner chamber of said first inflatable bladder and a second end connectable to a pump adapted to introduce said fluid into said inner chamber of said first inflatable bladder though said first fluid tube, said first fluid tube extending towards an ulnar side or a radial side of said supporting splint section.

4. The wrist-hand-finger orthosis according to claim 1, further comprising a first fluid tube having a first end in fluid connection with said inner chamber of said first inflatable bladder and a second end connectable to a pump adapted to introduce said fluid into said inner chamber of said first inflatable bladder though said first fluid tube, said first fluid tube extending along at least a portion of a palmar main surface of said supporting splint section, said palmar main surface is opposite to said dorsal main surface.

5. The wrist-hand-finger orthosis according to claim 1, wherein said second inflatable bladder is arranged on said dorsal main surface of said supporting splint section at said phalanx portion to be aligned with the proximal interphalangeal, PIP, joints and the distal interphalangeal, DIP, joints of said fingers.

6. The wrist-hand-finger orthosis according to claim 1, further comprising a second fluid tube having a first end in fluid connection with said inner chamber of said second inflatable bladder and a second end connectable to a pump adapted to introduce said fluid into said inner chamber of said second inflatable bladder though said second fluid tube, said second fluid tube extending along at least a portion of a distal-to-proximal length of said wrist and forearm splint section.

7. The wrist-hand-finger orthosis according to claim 1, further comprising a second fluid tube having a first end in fluid connection with said inner chamber of said second inflatable bladder and a second end connectable to a pump adapted to introduce said fluid into said inner chamber of said second inflatable bladder though said second fluid tube, said second fluid tube extending towards an ulnar side or a radial side of said supporting splint section.

8. The wrist-hand-finger orthosis according to claim 1, further comprising a second fluid tube having a first end in fluid connection with said inner chamber of said second inflatable bladder and a second end connectable to a pump adapted to introduce said fluid into said inner chamber of said second inflatable bladder though said second fluid tube, said second fluid tube extending along at least a portion of a palmar main surface of said supporting splint section, said palmar main surface is opposite to said dorsal main surface.

9. The wrist-hand-finger orthosis according to claim 1, wherein the convex surface of the planar sheet of said supporting splint section supports said hand and said fingers in a functional position.

10. The wrist-hand-finger orthosis according to claim 1, wherein said splint further comprises a thumb support connected to or integral with said supporting splint section.

11. The wrist-hand-finger orthosis according to claim 10, wherein said thumb support comprises:
a phalanx portion adapted to support the phalanges of said thumb; and
a connecting portion interconnecting said phalanx portion to said supporting splint section and adapted to support the metacarpal of said thumb.

12. The wrist-hand-finger orthosis according to claim 11, wherein said phalanx portion is separated with a distance along a dorsopalmar axis from a palmar main surface of said supporting splint section, said palmar main surface is opposite to said dorsal main surface.

13. The wrist-hand-finger orthosis according to claim 11, wherein said phalanx portion is angled relative to a palmar main surface of said supporting splint section, said palmar main surface is opposite to said dorsal main surface and the angle is within an interval of 120° and 150°.

14. The wrist-hand-finger orthosis according to claim 1, wherein said wrist and forearm splint section comprises:
a forearm portion to be aligned with said forearm and having a wire-based open frame structure; and
a wrist portion interconnecting said forearm portion and said supporting splint section.

15. The wrist-hand-finger orthosis according to claim 14, wherein said wrist portion is deformable at least in a portion adapted to be aligned with the wrist joint of said hand.

16. The wrist-hand-finger orthosis according to claim 1, further comprising a textile dress having an interior chamber adapted to house said splint and said first inflatable bladder, said textile dress comprises at least one opening providing access to a first fluid tube having a first end in fluid contact with said first inflatable bladder and a second fluid tube having a first end in fluid contact with said second inflatable bladder.

17. The wrist-hand-finger orthosis according to claim 16, further comprising multiple closing straps arranged along a distal-to-proximal axis of said textile dress with at least one closing strap arranged at a portion of said textile dress aligned with said supporting splint section when said splint is housed within said interior chamber of said textile dress and at least one closing strap arranged at a portion of said textile dress aligned with said wrist and forearm splint section when said splint is housed within said interior chamber of said textile dress, said multiple closing straps are arranged to secure said wrist-hand-finger orthosis to said hand and said forearm.

18. The wrist-hand-finger orthosis according to claim 1, wherein said splint is made as a unitary structure with said wrist and forearm splint section integral with said supporting splint section, said wrist-hand-finger orthosis further comprising multiple closing straps arranged along a distal-to-proximal axis of said splint with at least one closing strap arranged at said supporting splint section and at least one closing strap arranged at said wrist and forearm splint section, said multiple closing straps are arranged to secure said wrist-hand-finger orthosis to said hand and said forearm.

* * * * *

UNITED STATES PATENT AND TRADEMARK OFFICE
CERTIFICATE OF CORRECTION

PATENT NO. : 10,350,105 B2  
APPLICATION NO. : 14/859575  
DATED : July 16, 2019  
INVENTOR(S) : Thomas Eriksson Page 1 of 1

It is certified that error appears in the above-identified patent and that said Letters Patent is hereby corrected as shown below:

On the Title Page

Item (30) Foreign Application Priority Data, add "Sept. 22, 2014 (SE).......1451119-0".

Signed and Sealed this  
Third Day of September, 2019

Andrei Iancu  
*Director of the United States Patent and Trademark Office*